United States Patent [19]

Patterson

[11] 4,063,156

[45] Dec. 13, 1977

[54] ASSYMETRIC CYLINDER ELECTRON CAPTURE DETECTOR

[75] Inventor: Paul Louis Patterson, Walnut Creek, Calif.

[73] Assignee: Varian Associates, Inc., Palo Alto, Calif.

[21] Appl. No.: 662,064

[22] Filed: Feb. 27, 1976

[51] Int. Cl.² .......................................... G01N 27/00
[52] U.S. Cl. .................................................... 324/33
[58] Field of Search ................... 324/33; 250/374, 385, 250/423

[56] References Cited

U.S. PATENT DOCUMENTS

| | | | |
|---|---|---|---|
| 3,361,907 | 1/1968 | Gregory | 324/33 X |
| 3,378,725 | 4/1968 | Bochinski et al. | 324/33 X |
| 3,445,757 | 5/1969 | Krucoff | 324/33 |
| 3,478,205 | 11/1969 | Sporek | 324/33 X |
| 3,496,399 | 2/1970 | Buckingham et al. | 324/33 X |
| 3,634,754 | 1/1972 | Lovelock et al. | 324/33 |

Primary Examiner—Rudolph V. Rolinec
Assistant Examiner—Vincent J. Sunderdick
Attorney, Agent, or Firm—Stanley Z. Cole; Gerald M. Fisher; John M. Morrissey

[57] ABSTRACT

An asymmetric cylinder electron capture detector comprises an electrode configured to define an ionization volume, a source of ionizing radiation disposed within the ionization volume, a collector electrode, with a gas flowing past the collector electrode into the ionization volume. The electron current to the collector electrode provides an indication of the presence of electronegative constituents in the gas passing into the ionization volume. In order to provide wide dynamic range, the face of the collector electrode is disposed as close as possible to the electrode defining the ionization volume, yet is located so as to minimize field-free background current. The collector electrode and the electrode defining the ionization volume are each of cylindrical configuration, and are coaxially aligned but are spaced apart with respect to each other. The two electrodes are mechanically connected via an intermediately disposed cylindrical insulator cylinder. The collector electrode is received in one end of the insulator cylinder, and the electrode defining the ionization volume is received within the other end of the insulator cylinder. The collector electrode has an elongate portion extending into the interior of the insulator cylinder, but spaced apart from the inner surface of the insulator cylinder. This configuration provides a long insulative path to prevent electrical leakage between the electrodes. A transverse gas exit port is provided in that portion of the collector electrode within the insulator cylinder in order to impart turbulence to the flow of gas through the insulator cylinder into the ionization volume.

28 Claims, 2 Drawing Figures

ASSYMETRIC CYLINDER ELECTRON CAPTURE DETECTOR

FIELD OF THE INVENTION

This invention is a further development in the art of electron capture detectors, and relates in particular to an asymmetric cylinder electron capture detector suitable for use in both the dc mode and the pulsed mode.

DESCRIPTION OF THE PRIOR ART

An electron capture detector is particularly useful, for example, in measuring the electron absorptive properties of the effluent of a gas chromatograph, and for indicating the presence of an electronegative gas in leak detection applications.

An electron capture detector usually includes an electrode configured to define an ionization volume, with a source of ionizing radiation being disposed within the ionization volume. The source of ionizing radiation may be, for example, a tritiated foil of titanium or scandium, or a foil of nickel-63. A means is provided for passing a gas through the ionization volume. The charged particle emanations form the foil ionize the gas in the ionization volume, thereby producing secondary electrons having relatively low energies. The gas passing through the ionization volume may be, for example, the column effluent of a gas chromatograph or the sampled gas of a leak detector apparatus. A collector electrode is disposed in the vicinity of the ionization volume defining electrode.

A difference of electrical potential is provided between the collector electrode and the ionization volume defining electrode, thereby creating an electric field that causes the free electrons in the ionization volume to migrate toward the collector electrode. A means is provided for measuring the current of the migrating electrons. If the gas contains an electron-absorbing constituent, fewer electrons migrate to the collector than if no electron-absorbing constituent is present in the gas. Thus, measurement of the flow of electrons to the collector electrode can provide qualitative and quantitative information concerning electron-absorbing constituents in the gas.

Electron capture detectors have been made in a variety of configurations. Two particular configurations are those which have historically been designated as the "concentric cylinder" detector and the "asymmetric cylinder" detector. One reference discussing the prior art is an article by Dr. J. E. Lovelock, entitled "Analysis by Gas Phase Electron Absorption", which appeared in *Gas Chromatography* 1968, The Institute of Petroleum, London, 1969, pages 95–108.

A concentric cylinder detector for use in conjunction with a gas chromatographic apparatus typically comprises a cylindrical electrode structure housing a radioactive foil, and a cylindrical collector electrode disposed concentrically inside the electrode that houses the radioactive foil. Carrier and sample gases are caused to flow through the annular volume between the two electrodes. Charged particles emitted from the radioactive foil ionize the carrier gas inside the electrode structure housing the radioactive foil, thereby producing free electrons. Appropriate electronic circuitry causes a difference of electrical potential between the two electrodes, thereby causing the free electrons to migrate toward the collector electrode. A means is provided for measuring the flow, or current, of the free electrons.

An asymmetrical cylinder electron capture detector for use in conjunction with a gas chromatographic apparatus also typically comprises a cylindrical electrode structure housing a radioactive foil for ionizing the column effluent. A cylindrical collector electrode is likewise disposed coaxially with respect to the electrode structure housing the foil, but is displaced longitudinally from the interior of the foil-housing electrode structure. An electrically insulating cylinder mechanically connects the two electrodes so as to provide a flow path for the gaseous effluent, without permitting electrical conduction between the two electrodes. As in the case of the concentric cylinder detector, charged particles emitted by the radiation source ionize the carrier gas, thereby producing free electrons. Electronic circuitry is provided for causing these free electrons to migrate to the collector electrode, and for measuring the resulting electron current.

In general, the migration of free electrons can be accomplished in either a dc mode or a pulsed mode.

In the dc mode, a dc voltage is applied between the electrode housing the radiation source and the collector electrode. Variations in the continuously flowing current to the collector electrode are measured to obtain a quantitative indication of the amount of free electrons not absorbed by the sample gas constituents.

In the pulsed mode, voltage pulses of uniform width and amplitude are impressed across the electrode housing the radiation source and the collector electrode, while a separate generator produces a reference current. A frequency modulator is used to vary the rate of the voltage pulses, until the current to the collector electrode balances the reference current. The frequency required to balance the free electron current with the reference current provides a quantitative indication of the amount of electron-absorbing material present in the sample gas.

Both the pulsed mode of operation and the asymmetric cylinder configuration have considerable advantages. The pulsed mode operation, however, has not heretofore been used in commercial applications with electron capture detectors of asymmetric cylinder configuration, because pulse widths short enough to provide a satisfactory dynamic range could not be obtained.

The pulsed mode of operation provides a more nearly linear response than does the dc mode over a wider range of concentrations for electron-absorbing constituents in the sample gas. The asymmetric cylinder configuration provides a superior response to electron-absorbing constituents of the sample gas at higher electrode voltages than the concentric cylinder configuration.

If higher electrode voltages can be used to cause free electrons to migrate, the electron transit time between the electrode defining the ionization volume and the collector electrode is thereby reduced. The duration of the valtage pulses can thus be correspondingly reduced, thereby providing a wider dynamic range for the instrument. It is generally desirable that the pulse width be as small as possible, because the maximum variation in the pulse rate between zero and the rate at which the pulses begin to overlap is an inverse function of the pulse width. For a constant pulse amplitude, as the pulse width is reduced, energy can be imparted to the free electrons for shorter time durations. When the pulse widths are very narrow, each pulse endures for only a very short time. However, if the maximum transit time for the electrons from the ionization volume to the collector electrode is greater than the pulse width, all of the electrons cannot reach the collector electrode during the life of a single pulse. Thus, for short pulse widths, the measured current reaching the collector electrode may provide an erroneous indication of the actual concentration of electron-absorbing constituents in the sample gas.

Electron capture detectors have in the past been significantly affected by "field-free background current", which is a term used to designate an electron current that is independent of the current caused by the electronic circuitry. Field-free background current can result from a number of causes: e.g., high-energy beta particles from the radioactive foil that reach the collector electrode directly; charged particles that diffuse through the effluent to the collector electrode independently of the electric field; and/or charged particles that are carried to the collector electrode by convection of the moving gases. Field-free background current can vary with concentration of the sample gas in the effluent, thereby making a quantitative determination of the amount of electronegative material in the sample gas difficult to obtain.

The field-free background current is generally a greater problem in the pulsed mode than in the dc mode, because the pulses are generally off more than they are on. Since the field-free background current is not affected by the pulses, it tends to mask the current caused by migration of free electrons under the influence of the pulses. In the dc mode, the field-free background current, while inevitably present to some extent, is nevertheless a much smaller component of the total current detected than in the pulsed mode. The greater linearity of response provided by the pulsed mode, however, would make operation in the pulsed mode preferable, if the adverse features of pulsed mode operation experienced by the prior art, viz., the effects of field-free background current and the long electron transit times, could be overcome.

With the concentric cylinder configuration, the collector electrode is often directly exposed to the radioactive foil, thereby rendering the collector electrode susceptible to impact by the beta particles emitted by the radioactive foil. Also, in the concentric cylinder configuration, the collector electrode is generally surrounded by an ionized gas volume, thereby exposing the collector electrode to impact by diffusing or convecting charged particles.

Field-free background current can be reduced in the concentric cylinder electron capture detector by increasing the separation between the electrodes. This, however, reduces the dynamic range of the detector due to the larger electron transit distances and the correspondingly longer pulse widths required to provide sufficient energy to the electrons to enable the electrons to traverse such distances during the life of a single pulse. It has been found that electron transit times for the concentric cylinder detector can be reduced by using an argon-methane mixture as the carrier gas. A 90% argon - 10% methane mixture is effective in cooling free electrons to thermal energies, while still permitting them to have a high drift velocity in the electric field. However, the argon-methane mixture is more expensive and is more difficult to obtain than commonly used nitrogen as a carrier gas.

In the asymmetric cylinder electron capture detector, the collector electrode is generally positioned upstream of the radioactive foil so that the effluent flow is directed away from the collector electrode. By locating the collector electrode outside the ionization volume, direct impingement of beta particles on the collector electrode is minimized. The flow of the effluent gas away from the collector electrode minimizes the likelihood of charged particles, including negatively charged ions formed by the ionization process, reaching the collector electrodes by mass transport effects such as diffusion or convection. Thus, with respect to field-free background current, the asymmetric cylinder detector is superior to the concentric cylinder detector. However, asymmetric cylinder detectors known to the prior art required a long insulative path to maintain electrical isolation between the electrode defining the ionization volume and the collector electrode.

The long insulative path between the electrodes in prior art electron capture detectors resulted in long transit times for the free electrons, thereby reducing the dynamic response. Furthermore, in asymmetric electron capture detectors known to the prior art, the long insulative path required to prevent leakage between the electrodes was typically provided by an insulating ceramic cylinder of relatively large size. The size of the insulating cylinder provided a considerable surface area on which surface charge would accumulate as free electrons passed therethrough. Such surface charge would adversely affect the migration of electrons to the collector electrode, thereby introducing inaccuracy in the indication of the concentration of electron-absorbing constituents in the sample gas.

Heretofore, because of the disadvantages characteristic of the existing asymmetric cylinder electron capture detectors, as discussed above, their performance was not substantially improved by operation in the pulsed mode, and pulsed mode operation was confined to use with the concentric cylinder configuration.

SUMMARY OF THE INVENTION

This invention provides an asymmetric cylinder electron capture detector, which is suitable for operation in the pulsed mode as well as in the dc mode.

The electron capture detector of this invention comprises an electrode configured to define an ionization volume, a source of ionizing radiation disposed within the ionization volume, a collector electrode disposed externally of the ionization volume, means for causing a gas to flow past the collector electrode into the ionization volume, and means for applying a difference of electrical potential between the two electrodes. Both electrodes are ungrounded. The ionizing radiation causes the gas in the ionization volume to become ionized, and the difference of potential between the electrodes causes free electrons so formed to migrate toward the collector electrode. Electrical isolation of the electrodes is provided by a ceramic insulating structure disposed therebetween. In the preferred embodiment, the electrode defining the ionization volume, the insulating structure, and the collector electrode are all of generally cylindrical configuration, and are disposed coaxially with respect to each other. A feature of this invention is that the insulating structure mechanically connects the two electrodes in such a way that spacing between the electrodes is minimized, and the surface area of the insulating structure exposed for the accumulation of surface charge is also minimized.

The electrode defining the ionization volume is preferably, but not necessarily, of cylindrical configuration. The salient feature of the configuration of the electrodes of this invention is that the electrodes support an electric field, whose field pattern is substantially the same as the field pattern of an electric field that would be formed between a hypothetical first electrode of right-circular cylindrical configuration and a hypothetical second electrode of plate-like configuration disposed perpendicular to the axis of the first electrode at a position adjacent one end of the first electrode. The precise location of the face of the second electrode may be anywhere along the axis of the first electrode in the region extending from the precise end of the first electrode outward to a position away from the first electrode at which acceptable operation of the detector in the pulsed mode is still feasible. The concept of acceptable operation, with respect to the pulsed operating mode, is discussed hereinafter. The preferred configuration for the ionization-volume defining electrode of the invention is a right-circular cylindrical configuration. Nevertheless, it is anticipated that other electrode configurations may be suitable for certain particular applications.

In gas chromatographic applications, the effluent from a chromatographic column would be directed past the collector electrode structure into the electrode defining the ionization volume, and thence out from the electrode defining the ionization volume to effluent gas receiving means or, depending upon the kinds of gases involved, to atmosphere. A radioactive foil disposed within the ionization volume emits charged particles to ionize the effluent passing therethrough.

A cylindrically configured ceramic insulating structure mechanically connects the electrode defining the ionization volume with the collector electrode. The collector electrode in the preferred embodiment has an elongate portion extending substantially through the interior of the insulator to a point proximate the adjacent facing end of electrode defining the ionization volume. This elongate portion of the collector electrode has a smaller diameter than the interior of the insulator in the vicinity of the adjacent facing end of the ionization-volume defining electrode, so as to maintain a relatively small clearance therebetween. This configuration provides a relatively long insulative path to minimize electrical leakage between the collector electrode and the electrode defining the ionization volume, and provides a relatively short migration path for electrons from the interior of the ionization volume to the face of the collector electrode. The gap between the two electrodes is large enough to provide high electrical resistance, yet is short enough to provide relatively short transit times for electrons migrating to the collector electrode. The limited exposure of the interior surface of the insulator to charged particles minimizes the accumulation of surface charge on the insulator.

In the preferred embodiment, a transversely extending gas exit port is provided in the collector near the end of its elongate portion adjacent the radiation source. The transverse exit port causes effluent gas from the collector to be directed into the insulator at right angles to the overall direction of gas flow through the detector, thereby creating turbulence which inhibits the build-up of stagnant effluent gas in the insulator.

A feature of the detector of this invention is the minimal field-free background current. In particular, the impact on the collector electrode of beta particles in minimal because the collector electrode is not physically located within the ionization volume. Also, since gas flow is directed away from the collector electrode, the impact on the collector electrode of diffusing and convecting charged particles is likewise minimal.

For operation in the pulsed mode, the energy that drives the free electrons to the collector electrode is dependent upon the pulse width for a given constant pulse amplitude. In general, it is desirable to make the pulse width as short as possible in order to provide as wide a dynamic range as possible. As the average flight path, or transit time, of the free electrons from the ionization volume to the face of the collector electrode increases, the pulse width must necessarily also increase, for a given constant pulse amplitude, in order to provide sufficient energy to the electrons to permit their collection by the collector electrode during a single pulse. Thus, it is desirable, in terms of minimizing pulse width, to locate the collector electrode as close as possible to the adjacent facing end of the electrode defining the ionization volume. However, in terms of minimizing the field-free background current, the collector electrode should not enter into the ionization volume.

It has been found that for the preferred configuration of the electrodes and of the ceramic insulating structure, as described hereafter in greater detail in the specification, the field-free background current is reduced to such an extent that, for commercial purposes, the collector electrode can provide a satisfactory dynamic range, if the face of the collector electrode is located precisely at the adjacent facing end of the electrode defining ionization volume. It has also been found that, for nitrogen and for argon-methane carrier gases, a satisfactory dynamic range can likewise be obtained if the collector electrode is located coaxially spaced apart from the adjacent facing end of the electrode defining the ionization volume, provided that the separation between the electrodes is short enough so that the free electrons can travel to the collector electrode during a pulse width of one microsecond or less. Thus, for specialized applications in which a narrower dynamic range can be tolerated in order to reduce field-free background current to its lowest possible extent, the collector electrode of this invention can be located coaxially spaced apart from the adjacent facing end of the ionization-volume defining electrode. However, the separation of the face of the collector electrode from the adjacent facing end of the electrode defining the ionization volume can be no more than that which provides an "acceptable" trade-off between reduced field-free background current and reduced dynamic range. Preliminary experiments by the inventor indicate that such coaxial separation would in most cases not exceed 0.125 inch (approximately 0.32 cm).

Particularly suitable electronic circuitry for operating the electron capture detector of this invention in the pulsed mode is disclosed in copending patent application Ser. No. 661,467 by John R. Felton and Russell S. Gutow, filed February 1976, and assigned to the assignee of the present invention.

The achievement of lower electron transit times improves the dynamic range of the asymmetric cylinder electron capture detector in the pulsed mode. The dynamic range of the detector of the present invention has been found to be about 10, using sulphur hexafluoride as the sample gas and using nitrogen as the carrier gas.

With the detector of this invention, the linearity of response with respect to pulsed frequency of the concentration of electron-absorbing constituents in the sample gas continues practically up to the dc limit, which is the point at which the pulses begin to overlap and become an essentially uninterrupted dc signal. Thus, it is a general object of this invention is to provide an asymmetric cylinder electron capture detector that is capable of implementing the advantages of linear operation in the pulsed mode, while exhibiting low field-free background current and a wide dynamic range.

Other objects and advantages of the present invention may be discerned from the following detailed specification in conjunction with the accompanying drawing and appended claims.

DESCRIPTION OF THE PREFERRED EMBODIMENT

Figure 1:
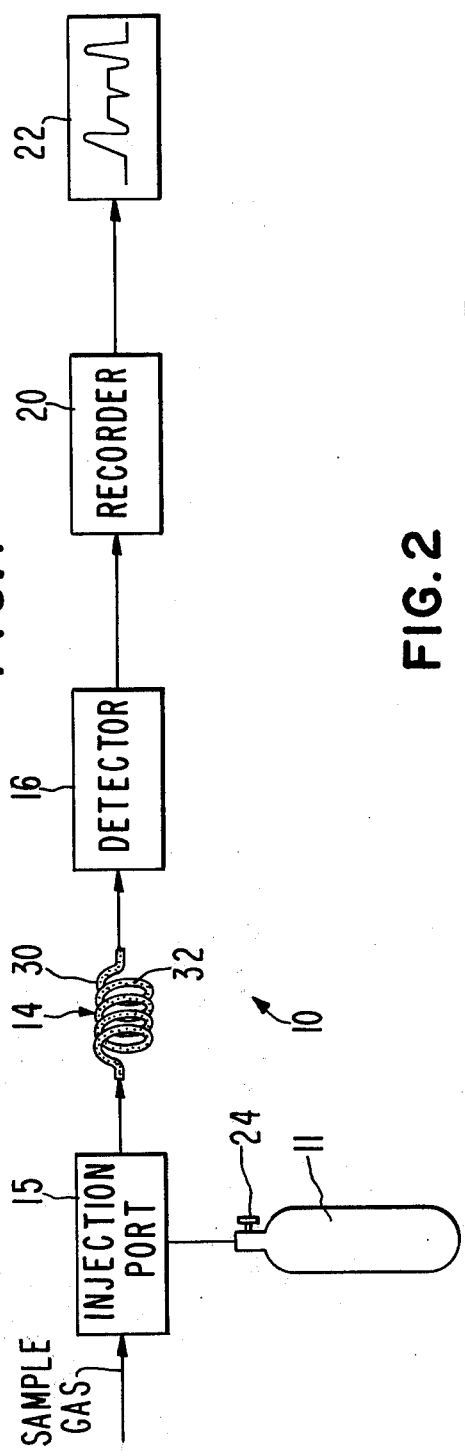
FIG. 1 is a diagrammatic view of a gas chromatographic system incorporating the asymmetric cylinder electron capture detector of this invention.

FIG. 1 shows a gas chromatographic system 10, which incorporates the asymmetric electron capture detector of this invention.

The system 10 includes a pressurized container 11 for storing a supply of carrier gas, such as nitrogen. The container 11 delivers a stream of carrier gas to a chromatographic column 14. A quantity of sample gas is added to the carrier gas stream via an injection port 15 located in a conduit between the container 11 and the column 14. Stationary phase material within the column 14 adsorbs some or all of the constituents of the sample gas in varying degrees, such that the effluent from the column 14 exhibits a particular measurable property that is a time-varying function of the nature and amount of the constituents of the sample gas. A detector 16 senses variations in this measurable property of the effluent, and actuates a recorder 20 for providing a permanent record 22 of the time variations of this measurable property.

The carrier gas supply container 11 is highly pressurized, and is preferably made of steel. It is a feature of this invention that the detector 16 performs well using relatively inexpensive and widely available nitrogen as the carrier gas. A more costly argon-methane gas mixture can also be used, but is not necessary for achieving a dynamic range as wide as 10 for an electronegative gas such as sulphur hexafluoride. The carrier gas supply container 11 may also include a flow meter 24 for adjusting the rate of flow of the carrier gas toward the column 14.

The injection port 15 may comprise any suitable type of device known to those skilled in the art for injecting the sample gas into the high-pressure carrier gas stream flowing between the carrier supply container 11 and the column 14.

The column 14 likewise may be of a type known to those skilled in the art, and comprises an elongate tubular portion 30 containing a stationary phase material 32. The mixture of carrier gas and sample gas percolates through the stationary phase 32 within the tubular portion 30. The stationary phase 32 is a liquid or solid material chosen for its property of differentially adsorbing certain substances, preferably the anticipated constituents of the sample gas. By reason of such differential adsorption, at least one property of the effluent from the column 14 is caused to vary as a function of time, the time function being related to the capability of the stationary phase 32 to adsorb the constituents of the sample gas.

One property of the effluent which varies by the action of the stationary phase on the effluent is the capability of the effluent, when ionized, to capture free electrons.

The detector 16, which is of the electron capture type, receives and analyzes the column effluent. The effluent passing through the detector 16 is ionized so as to generate free electrons, which are thereupon formed into a measurable electron current by an impressed electric field. Fluctuations in this measurable electron current are indicative of variations in the capability of the sample gas to capture free electrons. Thus, fluctuations in the electron current can provide a quantitative measurement of the presence of electronegative constituents in the sample gas.

The recorder 20 is connected by suitable electronic circuitry to the detector 16 so as to indicate the time-varying capability of the ionized effluent to capture free electrons. The recorder 20, which is preferably a strip chart recorder, produces a permanent strip chart recording 22 indicating the time variations in the capture of free electrons.

Figure 2:
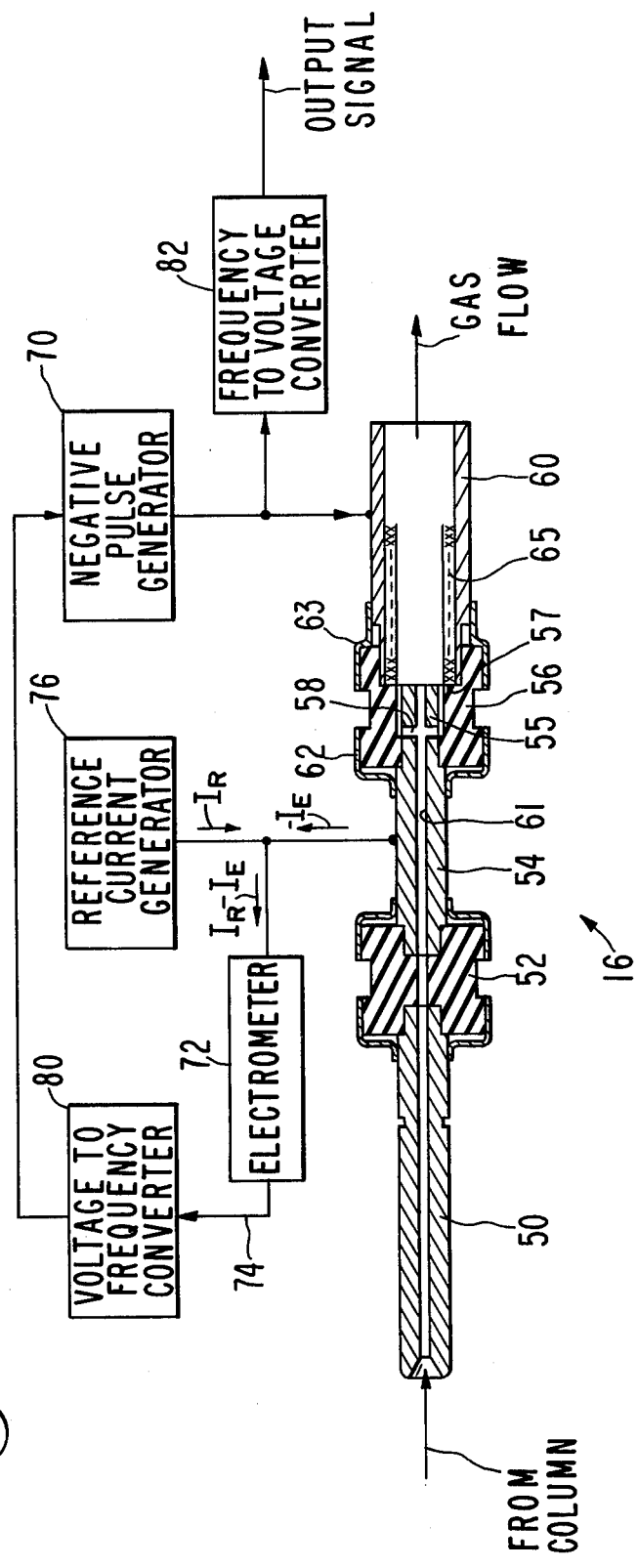
FIG. 2 is an elevational view, partially in block form, showing the electron capture detector portion of the system of FIG. 1.

FIG. 2 illustrates in detail the structure of the detector 16, and provides a functional representation of the associated electronic circuitry. Effluent gas from the column 14 is supplied to the detector 16 by way of a feed tube 50. The effluent gas is directed through a first tubular insulator 52 connecting the feed tube 50 with a generally cylindrical collector electrode structure 54. The collector electrode 54 extends from the first insulator 52 to a second tubular insulator 56. The effluent flowing through the collector electrode 54, and thence through the second insulator 56, is directed toward a tubular radiation source cell 60. The radiation source cell 60 and the collector electrode 54 are aligned coaxially with and longitudinally spaced apart from one another. The second insulator 56 provides gas communication between the collector electrode 54 and the radiation source cell 60. The insulators 52 and 56 maintain the source cell 60 and the collector electrode 54 isolated electrically from ground and from each other.

The insulator 52 is preferably made of an electrically insulating ceramic material having sufficient rigidity to support the facing ends of the feed tube 50 and the collector electrode 54 in fixed relationship with respect to one another. The collector electrode 54 is preferably a metallic cylindrical member having a bore 61, which provides gas communication between the interiors of the first insulator 52 and the second insulator 56. The collector electrode 54 is made of electrically conductive material, such as stainless steel or Kovar metal. The insulator 56 is similar to the insulator 52 in configuration and material. The insulator 56 holds the adjacent ends of the collector electrode 54 and the tubular radiation source cell 60 in fixed relationship with respect to one another. The collector electrode 54 thus provides gas communication from the feed tube 50 and the insulator 52 to the insulator 56 and the interior of the radiation source cell 60.

The radiation source cell 60 is of generally hollow cylindrical configuration. A source 65 of ionizing radiation, such as a foil of tritiated titanium or scandium, or a foil of nickel-64, is disposed adjacent the interior surface of the radiation source cell 60. The radioactive foil 65 irradiates the effluent gas flowing through the cell 60 with charged particles, thereby ionizing the effluent gas so as to generate free electrons.

Electron circuitry is connected to the radiation source cell 60 and to the collector electrode 54 for establishing an electric field so as to cause the free electrons generated by the ionization process to migrate toward the collector electrode 54, (i.e., in the direction contrary to the direction of gas flow), and to measure the rate of such electron migration. Suitable circuitry for producing an electric field includes a negative pulse generator 70, which is connected to the conductive material comprising the radiation source cell 60. The negative pulse generator 70 produces pulses of negative voltage, and impresses these pulses on the radiation source cell 60. The pulses are uniform in width, being approximately 0.6 microseconds in duration. The negative pulse generator 70 is of a known type, and includes means for adjusting the frequency of the negative pulses impressed upon the cell 60.

The impression of a negative pulse on the cell 60 establishes an electric field, which causes the free electrons produced by the ionization process to migrate toward the collector electrode 54. The collector electrode 54 thus receives a negative charge flow, which is a function of the rate at which the free electrons migrate from the cell 60 to the collector electrode 54, and of the fraction of free electrons absorbed by the effluent gas.

A direct current electrometer 72 is connected to the collector electrode 54 in order to measure the flow of the migrating free electrons. The electrometer 72 is a known type of instrument for accurately measuring minute current flow. The free electron current $(-I_E)$ from the collector electrode 54 is combined at the input of electrometer 72 with a reference current $(I_R)$ that is generated by a dc reference current generator 76. The electrometer 72 amplifies the $I_R$-$I_E$ signal, and produces a signal on a lead 74 which is a function of the current difference $I_R$-$I_E$.

A voltage-to-frequency converter means 80 causes the negative pulse generator 70 to produce pulses with a frequency dependent upon the voltage signal on the electrometer output lead 74. The pulse frequency of the negative pulse generator 70 is adjusted until the current difference, $I_R$-$I_E$, becomes zero. A frequency-to-voltage converter 82 produces an output signal proportional to the pulse frequency output of the negative pulse generator 70. The frequency of the pulses impressed on the radiation source cell 60 is thus utilized as an indication of the concentration of electron-absorbing constituents in the sample gas.

The insulator 56 is configured so that one end thereof overlaps an adjacent end of the collector electrode 54, and the other end thereof overlaps an adjacent end of the radiation source cell 60. Thus, the adjacent ends of the collector electrode 54 and radiation source cell 60 are received within the insulator 56. A caping member 62 fits over and coaxially surrounds the overlapping ends of the insulator 56 and the collector electrode 54. Similarly, a caping member 63 fits over and coaxially surrounds the overlapping ends of the insulator 56 and the radiation source cell 60. The caping members are bonded to the members they join, as by brazing, in order to provide a gas-tight seal. In a similar manner, the insulator 52 is sealed to the feed tube 50 and to the other end of the collector electrode 54.

The collector electrode 54 has an elongate portion 55 extending longitudinally into the interior of the insulator 56. The elongate portion 55 does not contact the interior surface of the radiation source cell 60, but rather has an outside diameter that is smaller than the inside diameter of the insulator 56, thereby precluding physical contact therebetween. This configuration minimizes electrical leakage between the collector electrode 54 and the radiation source cell 60 by providing a relatively long insulative path from the radiation source cell 60, received in one end of the insulator 56, to that portion of the collector electrode 54 which is in contact with the insulator 56 at the other end thereof. The outstanding feature of this configuration is that the spacing between the radiation source cell 60 and the face of the collector electrode 54 can be minimized, while still providing a relatively long insulative path between the electrodes to minimize electrical leakage therebetween.

It is generally desirable, from the standpoint of achieving wide dynamic range, to minimize the transit time required for free electrons generated in the ionization volume to migrate to the face of the collector electrode 54. Thus, it is generally desirable to locate the face of the collector electrode 54 as close as possible to the facing end of the radiation source cell 60. In the preferred embodiment shown in FIG. 2, the elongate portion 55 of the collector electrode 54 extends into the interior of the insulator 56 to a terminus coplanar with the facing end of the radiation source cell 60. The resulting electric field pattern is substantially the same, for purposes of mathematical analysis, as the field formed between a right-circular cylindrical electrode of one polarity and a plate-like electrode of opposite polarity disposed perpendicular to the axis of the cylindrical electrode at a position adjacent one end of the cylindrical electrode.

It is recognized that the close proximity of the face of the collector electrode 54 to the ionization volume, as shown in FIG. 2, theoretically renders the collector electrode 54 more susceptible to field-free background current, due to direct bombardment by beta particles from the ionization source 65, and due to the impingement of negatively charged particles carried thereto by mass transport phenomena such as diffusion and convection, than would occur if the face of the collector electrode 54 were disposed further away from the facing end of the radiation source cell 60. It has been found, however, that for commercial applications, the disposition of the collector electrode 54 with respect to the radiation source cell 60, as shown in FIG. 2, is for the most part untroubled by the field-free background current problem that plagued concentric cylinder electron capture detectors in the prior art.

For particular specialized applications where the field-free background current must be reduced to the greatest possible extent, even at the expense of dynamic range, the terminus of the elongate portion 55 of the collector electrode 54 need not extend into the interior of the insulator 56 quite so far as shown in FIG. 2. The face (i.e., the terminus) of the elongate portion 55 could be spaced apart from the plane defining the facing end of the radiation source cell 60 by whatever amount is necessary to accomplish the desired ultra-minimization of field-free background current while still providing feasible pulsed mode operation.

Investigations by the inventor indicate that feasible operation of the detector of this invention in the pulsed mode would require that the separation between the end of the elongate portion 55 of the collector electrode 54 and the plane defining the facing end of the radiation source cell 60 be not greater than about 0.125 inch (0.32 cm). Greater separation than that would require pulse widths of longer than one microsecond in order to permit the electrons to travel from the ionization volume to the collector electrode 54 during a single pulse. Such long pulse widths would severely limit the dynamic range of the instrument, and would therefore severely limit the utility of the instrument for large sample concentrations. The maximum pulse frequency that could be impressed on the radiation source cell 70 is that frequency at which the pulses overlap. The wider the pulse width is, the lower is the frequency at which the pulses overlap. Thus, any lowering of the dynamic range lowers the sample concentration for which the instrument can be effective.

The bore 61 extends axially throughout the entire length of the collector 54, thereby providing gas communication from the chromatographic column, via the feed tube 50 and the insulator 52, to the interior of the cell 60. In the preferred embodiment, the elongate portion 55 has a transverse gas exit port 58 for directing the effluent gas into the interior of the insulator 56 at right angles to the bore 61. This configuration causes gas turbulence within the insulator 56, which prevents the accumulation of stagnant effluent gas and minimizes the build-up of surface charge on the interior surface of the insulator 56. Thus, the likelihood of spurious output signals being generated by delayed passage to the radiation source cell 60 of sample gas that has been detained in the insulator 56 is minimized.

The detector described above is an asymmetric cylinder electron capture detector suitable for use in the pulsed mode, and is capable of achieving the advantages normally associated with pulsed mode operation. This detector possesses favorable linearity of response and low fluid-free background current, which are characteristics of asymmetric cylinder detectors generally, and in addition provides the shorter electron transit times required for good dynamic range.

Although the primary advantages of this detector are associated with operation in the pulsed mode, it is to be emphasized that this detector also performs well in the dc mode.

This detector can also be used in leak detection and related applications. It can be employed in any application requiring detection of electronegative sample gases contained in a non-electronegative carrier gas. For example, electron capture detectors are frequently used in leak detection apparatus where electron-absorbing gases are employed to pinpoint leaks in pneumatic systems. In a particular application, the gas that is caused to flow through the collector electrode into the ionization volume is gathered from one side of an object to be leak tested. An electronegative gas such as sulphur hexafluoride is then introduced to the other side of the object to be leak tested. When a leak occurs, the electronegative gas passes through the leak, and can be detected as a constituent of the gas passing through the ionization volume.

The description of the embodiment set forth above is intended to be illustrative rather than exhaustive of the present invention. It should be appreciated that those of ordinary skill in the art may make certain modifications, additions or changes to the described embodiment without departing from the spirit and scope of this invention as claimed hereinafter.

What is claimed is:

1. An electron capture detector comprising a first electrode defining an ionization volume, a collector electrode disposed externally of said ionization volume, means for allowing a gas to flow past said collector electrode into said ionization volume, means for ionizing the gas in said ionization volume, and electrical pulse generating means connected to said electrodes for causing free electrons in said ionization volume to migrate to said collector electrode during a pulse, said electrodes being coaxially disposed with respect to each other, one end of said collector electrode being spaced apart from one end of said first electrode by no more than 0.125 inch.

2. The electron capture detector of claim 1 wherein said one end of said first electrode defines a plane, and wherein said one end of said collector electrode is coplanar with said one end of said first electrode.

3. The electron capture detector of claim 1 wherein said electrodes are of cylindrical configuration and are electrically isolated from each other by a generally cylindrical insulator structure.

4. The electron capture detector of claim 3 wherein said collector electrode is received within one end of said insulator structure, and wherein said first electrode is received within the other end of said insulator structure, said electrodes and said insulator structure being configured to provide a flow path for gas in a direction from said collector electrode through said insulator structure into said ionization volume.

5. The electron capture detector of claim 4 wherein said collector electrode has an elongate portion extending into the interior of said insulator structure, said elongate portion being spaced apart from the interior surface of said insulator structure.

6. The electron capture detector of claim 5 wherein said elongate portion of said collector electrode extends into the interior of said insulator structure to a position coplanar with said one end of said first electrode.

7. The electron capture detector of claim 5 wherein said elongate portion of said collector electrode defines a gas exit port for directing gas from the interior of the collector electrode into the insulator structure in a direction transverse to the axis of said insulator structure, whereby turbulence is induced in said gas.

8. An electron capture detector comprising a first electrode defining an ionization volume, a collector electrode disposed externally of said ionization volume, means for allowing a gas to flow past said collector electrode into said ionization volume, means for ionizing said gas within said ionization volume, and means connected to said electrodes for generating a sequence of electrical pulses for causing free electrons in said ionization volume to migrate to said collector electrode, said electrodes being spaced apart from each other by a distance no greater than that distance which will permit all free electrons in said ionization volume to migrate to said collector electrode during a single pulse of one microsecond duration.

9. An electron capture detector comprising a first electrode defining an ionization volume, a collector electrode disposed externally of said ionization volume, one end of said first electrode defining a plane and one end of said collector electrode being coplanar with said one end of said first electrode, means for allowing a gas to flow past said collector electrode into said ionization volume, means for ionizing said gas within said ionization volume, and means connected to said electrodes for generating a sequence of electrical pulses for causing free electrons in said ionization volume to migrate to said collector electrode, said electrodes being spaced apart from each other by a distance no greater than that distance which will permit all free electrons in said ionization volume to migrate to said collector electrode during a single pulse.

10. An electron capture detector comprising a first electrode defining an ionization volume, a collector electrode disposed externally of said ionization volume, said electrodes being of cylindrical configuration and being electrically isolated from each other by a generally cylindrical insulator structure, means for allowing a gas to flow past said collector electrode into said ionization volume, means for ionizing said gas within said ionization volume, and means connected to said electrodes for generating a sequence of electrical pulses for causing free electrons in said ionization volume to migrate to said collector electrode, said electrodes being spaced apart from each other by a distance no greater than that distance which will permit all free electrons in said ionization volume to migrate to said collector electrode during a single pulse.

11. The electron capture detector of claim 10 wherein said collector electrode is received within one end of said insulator structure, and wherein said first electrode is received within the other end of said insulator structure, said electrodes and said insulator structure being configured to provide a flow path for gas in a direction from said collector electrode through said insulator structure into said ionization volume.

12. The electron capture detector of claim 11 wherein said collector electrode has an elongate portion extending into the interior of said insulator structure, said elongate portion being spaced apart from the interior surface of said insulator structure.

13. The electron capture detector of claim 12 wherein said elongate portion of said collector electrode extends into the interior of said insulator structure to a position coplanar with said one end of said first electrode.

14. The electron capture detector of claim 12 wherein said elongate portion of said collector electrode defines a gas exit port for directing gas from the interior of the collector electrode into the insulator structure in a direction transverse to the axis of said insulator structure, whereby turbulence is induced in said gas.

15. An asymmetric cylinder electron capture detector comprising a generally cylindrical collector electrode, a generally cylindrical structure housing a source of ionizing radiation, and a generally cylindrical electrical insulator disposed intermediate said collector electrode and said radiation source housing structure; said collector electrode, insulator, and radiation source housing structure being generally coaxially aligned and being configured to provide a flow path for gas therethrough in a direction through said collector electrode toward said radiation source housing structure via said insulator; said collector electrode having an elongate portion extending into the interior of said insulator to substantially preclude the formation of surface charge on the surface of said insulator; and means for providing an electric field to cause free electrons produced by ionization of gas in said radiation source housing structure to migrate toward said collector electrode.

16. The electron capture detector of claim 15 further comprising means for measuring the rate of migration of free electrons toward said collector electrode.

17. The electron capture detector of claim 15 wherein said source of ionizing radiation is a foil structure mounted within said radiation source housing structure.

18. The electron capture detector of claim 17 wherein said foil structure comprises tritiated titanium.

19. The electron capture detector of claim 17 wherein said foil structure comprises tritiated scandium.

20. The electron capture detector of claim 17 wherein said foil structure comprises nickel-63.

21. The electron capture detector of claim 15 wherein said elongate portion of said collector electrode has a smaller diameter than the interior of said insulator so as to maintain a clearance therebetween.

22. The electron capture detector of claim 15 wherein said elongate portion of said collector electrode defines a gas exit port configured so as to direct gas from the collector electrode into the insulator in a direction transverse to the axis of said insulator, whereby turbulence is induced in said gas.

23. The electron capture detector of claim 15 further comprising means for mechanically coupling said collector electrode to a gas chromatograph column, whereby effluent from said column can flow through said collector electrode toward said radiation source housing structure.

24. The electron capture detector of claim 15 wherein said means for providing said electric field comprises means for producing a pulsed electric field.

25. The electron capture detector of claim 15 wherein said means for providing said electric field comprises means for producing a continuous electric field.

26. The electron capture detector of claim 15 wherein said collector electrode and said radiation source housing structure are both ungrounded.

27. The electron capture detector of claim 24 wherein said means for producing a pulsed electric field comprises a negative pulse generator connected to said radiation source housing structure, and an electrometer connected to said collector electrode, said negative pulse generator being electrically coupled to said electrometer via a voltage-to-frequency converter so as to vary the frequency of said pulse generator in response to the output voltage of said electrometer.

28. A method for analyzing effluent gas from a chromatographic column by means of an electron capture detector having a collector electrode, a structure housing a source of ionizing radiation, and an electrical insulator disposed between said collector electrode and said radiation source housing structure, said collector electrode, insulator and radiation source housing structure being of generally cylindrical configuration and being coaxially aligned with but longitudinally separated from one another, said method comprising the steps of:
  a. introducing the effluent to the collector electrode along a flow path directed toward the radiation source housing structure;
  b. conducting the effluent along a closed conduit substantially through the insulator;
  c. expelling at least a portion of the effluent from said conduit into the insulator near the radiation source housing structure at an angle transverse to the flow path of the effluent through the collector;
  d. irraditaing the effluent within the radiation source housing structure to release free electrons;
  e. causing such free electrons to migrate toward the collector; and
  f. measuring the rate of said free electron migration.

* * * * *

UNITED STATES PATENT AND TRADEMARK OFFICE
CERTIFICATE OF CORRECTION

PATENT NO. : 4,063,156
DATED : December 13, 1977
INVENTOR(S) : Paul Louis Patterson It is certified that error appears in the above-identified patent and that said Letters Patent are hereby corrected as shown below:

Column 2, line 40, after "mode" insert --of--;
Column 2, line 57, change "valtage" to --voltage--;
Column 5, line 65, change "in" to --is--;
Column 6, line 62, change "10" to $--10^6--$;
Column 7, line 47, change "10" to $--10^6--$;
Column 8, line 66, change "nickel-64" to --nickel-63--;
Column 11, line 35, change "fluid-free" to --field-free--.

Signed and Sealed this

Fourteenth Day of April 1981

[SEAL]

Attest:

RENE D. TEGTMEYER

Attesting Officer   Acting Commissioner of Patents and Trademarks